United States Patent [19]

Matz et al.

[11] Patent Number: 5,338,541
[45] Date of Patent: Aug. 16, 1994

[54] DUAL CATIONIC TERPOLYMERS PROVIDING SUPERIOR CONDITIONING PROPERTIES IN HAIR, SKIN AND NAIL CARE PRODUCTS

[75] Inventors: Gary F. Matz, Rosslyn Farms; Craig Vaughan, Freedom, both of Pa.

[73] Assignee: Calgon Corporation, Pittsburgh, Pa.

[21] Appl. No.: 961,574

[22] Filed: Oct. 15, 1992

[51] Int. Cl.$^5$ .................. A61K 7/11; A61K 7/04
[52] U.S. Cl. ...................... 424/71; 424/70; 424/61; 424/47; 424/59; 424/73; 514/844
[58] Field of Search ............ 424/70, 71, 401, 47

[56] References Cited

U.S. PATENT DOCUMENTS

| | | | |
|---|---|---|---|
| 3,986,825 | 10/1976 | Sokol | 8/10.1 |
| 4,065,422 | 12/1977 | Lundmark et al. | 260/29.6 |
| 4,128,631 | 12/1978 | Lundmark et al. | 424/70 |
| 4,131,576 | 12/1978 | Iovine et al. | 260/17.4 |
| 4,175,572 | 11/1979 | Hsiung et al. | 132/7 |
| 4,455,240 | 6/1984 | Costello | 252/8.5 |
| 4,460,477 | 7/1984 | Costello et al. | 210/701 |
| 4,484,631 | 11/1984 | Sherwood et al. | 166/274 |
| 4,533,708 | 8/1985 | Costello | 526/295 |
| 4,590,249 | 5/1986 | Cabestany | 424/70 |
| 4,710,374 | 12/1987 | Grollier et al. | 424/61 |
| 4,719,104 | 1/1988 | Patel | 424/70 |
| 4,803,071 | 2/1989 | Iovine et al. | 424/70 |
| 4,832,872 | 5/1989 | Scandel | 252/547 |
| 4,842,849 | 6/1989 | Grollier et al. | 424/70 |
| 4,859,458 | 8/1989 | Salamone et al. | 424/70 |
| 4,898,725 | 2/1990 | Hoeffkes et al. | 424/70 |
| 5,147,635 | 9/1992 | Jachowicz | 424/70 |

FOREIGN PATENT DOCUMENTS

| | | | |
|---|---|---|---|
| 0139588 | 5/1985 | European Pat. Off. | 424/70 |
| 0227321 | 12/1985 | European Pat. Off. | |
| 0246090 | 5/1986 | European Pat. Off. | |
| 0270250 | 11/1986 | European Pat. Off. | |
| 0308189 | 9/1987 | European Pat. Off. | |
| 0308190 | 9/1987 | European Pat. Off. | |
| 0353987 | 8/1988 | European Pat. Off. | |

OTHER PUBLICATIONS

Sykes et al., The Use of Merquat Polymers in Cosmetics, Feb. 1980 vol. 126, pp. 62, 64, 66, 68, 126.

*Primary Examiner*—Thurman K. Page
*Assistant Examiner*—Sally Gardner
*Attorney, Agent, or Firm*—Craig G. Cochenour; William C. Mitchell; Michael J. Kline

[57] ABSTRACT

Terpolymers with more than one constituent cationic monomer, further copolymerized with acrylamide, are conditioning additives for hair, skin and nail care products which, with regard to hair, improve wet and dry hair combability, especially detangling and reduced static flyaway, sheen, and fixative properties, especially curl retention, and with regard to skin and nails, improve softening or lubricating (lubricity), moisture retention and attraction (moisturizing), feel, and reduction of irritation. The dual cationic polymers may have a weight average molecular weight of from about 10 thousand to 10 million, and comprise (a) from at least 30 to as much as 75 weight percent of acrylamide (AM), (b) from at least 25 to as much as 80 weight percent of the cationic monomer dimethyldiallylammonium chloride (DMDAAC), and (c) from at least 5 to as much as 35 weight percent of a second cationic monomer of the formula:

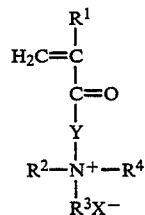

where Y is —O—A— or —NH—A—, where A is ethyl or propyl; $R^1$ is H or $CH_3$; $R^2$, $R^3$ and $R^4$ are independently selected from H and $C_{1-12}$alkyl; and $X^-$ is a suitable anion, especially $^-Cl$ and $^{-OSO_3}CH_3$.

8 Claims, No Drawings

DUAL CATIONIC TERPOLYMERS PROVIDING SUPERIOR CONDITIONING PROPERTIES IN HAIR, SKIN AND NAIL CARE PRODUCTS

BACKGROUND OF THE INVENTION

1. Field of the Invention

The present invention relates to compositions and methods for treating hair, as well as the skin and nails, in which a cosmetically acceptable medium is used which contains from 0.1–10% by weight of a dual cationic terpolymer described in detail further below.

HAIR CARE PRODUCTS

The first aspect of the utilization of the compositions and methods of the present invention is with respect to providing superior conditioning properties in shampoos and other hair care products.

The surface properties of human hair are, of course, of basic interest in cosmetic science, and there has thus been a long-standing desire to discover ingredients which will beneficially affect the topical and bulk condition of this keratinous substrate. Such ingredients must have adequate adherent properties, so that they are not only adsorbed initially, but are also retained on exposure to water. This property is referred to as "substantivity", i.e., the ability of a material to be adsorbed onto the keratin of the hair and to resist removal by water rinse-off.

As indicated, human hair is composed of keratin, a sulfur-containing fibrous protein. The isoelectric point of keratin, and thus of the hair of which it is composed, is in the pH range of 3.2–4. Thus, at the pH of typical shampoo conditions, hair carries a net negative charge. Consequently, cationic polymers have long been used as conditioners in shampoo formulations, or as a separate treatment, in order to improve the wet and dry combability of the hair. The substantivity of the cationic polymers for negatively charged hair leads to film formation that facilitates detangling in wet hair combing and a reduction in static flyaway in dry hair combing. The cationic polymers also impart softness and suppleness to the hair.

When cationic polymers are added to shampoos containing anionic surfactants, formation of highly surface active association complexes takes place which imparts improved foam stability to the shampoo. Maximum surface activity and foam stability, or lather, are achieved at near stoichiometric ratios of anionic sufactant:cationic polymer, where the complex is least water soluble. All cationic conditioners exhibit some incompatibility at some of these ratios. Compatibility gives a commercially more desirable clear formulation, while incompatibility leads to a haze or precipitation, which is aesthetically less desirable.

Hair fixative properties such as curl retention, are directly related to the film forming properties of the cationic monomers, as well as to molecular weight, with performance increasing with increasing molecular weight. However, the fixative properties conferred by the cationic monomers tend to have a reciprocal relationship to the other conditioning properties, i.e., good curl retention means that wet combability, for example, will suffer, and vice versa.

Surprisingly, it has been found that it is possible, using the dual cationic terpolymers of the present invention, to retain a desired balance of beneficial conditioning properties. Thus, it is possible to keep the desired properties of substantivity, combability and feel, while at the same time improving anionic surfactant compatibility, curl retention, sheen, and static reduction properties.

As already indicated, it is a preferred embodiment of the present invention to add the dual cationic terpolymers directly to an anionic surfactant-containing shampoo. Other embodiments are contemplated, however. Thus, excellent results have been achieved with treatments usually followed by rinsing, such as shampooing, but have also been achieved with treatments with lotions or creams followed by rinsing, which are used to obtain hair-conditioning effects and are applied before or after coloring, bleaching, shampooing, perming or straightening.

Thus, the compositions according to the present invention can also be used in the form of coloring products, setting lotions, blow-drying lotions, restructuring lotions or bleaching, perming or straightening products.

SKIN AND NAIL CARE PRODUCTS

The other aspect of utilization of the compositions and methods of the present invention is with respect to providing superior conditioning properties in skin and nail care products.

The surface properties of human skin and nails are, of course, of basic interest in cosmetic science, and there has thus been a long-standing desire to discover ingredients which will beneficially affect the topical condition of this keratinous substrate. Skin conditioning products are desired which will function to improve such properties as retention of skin moisture, softening of the skin, attraction of air moisture, retardation of skin water loss, feel and reduction of skin irritations caused by contact with detergents, soaps and the like.

In this field, two broad areas of skin care products have been recognized as skin conditioners: emollients and humectants. Emollients function to provide improved moisture retention in the skin and plasticization/softening of the skin. Common commercial emollients are mineral oil; petrolatum; aliphatic alcohols,, such as stearyl alcohol; lanolin and its derivatives; glycol stearate; and fatty acids, such as triethanolamine oleate. Humectants function to attract moisture, retard evaporation of water from the skin surface, and plasticize/soften skin. Common commercial humectants are glycerin, propylene glycol, sorbitols, and polyethylene glycols.

A desirable skin conditioner should impart all or some of the attributes of an emollient and a humectant, as well as provide improved lubricity and feel to the skin after treatment and/or reduce skin irritation caused by other components in the conditioner such as soaps, detergents, foam boosters, surfactants, perfumes and the like. Recently, cationic polymers have been used as skin conditioners.

Sometimes, it is also desirable that the ingredients of skin and nail care products will have adequate adherent properties, so that they are not only adsorbed initially, but are also retained on exposure to water. This property is referred to as "substantivity", i.e., the ability of a material to be adsorbed onto the keratin of the skin and nails and to resist removal by water rinse-off.

As indicated, human skin and nails are composed of keratin, a sulfur-containing fibrous protein. The isoelectric point of keratin, and thus of the hair of which it is composed, is in the pH range of 3.2–4. Thus, at the pH of typical use conditions, the human skin and nails carry a net negative charge. Consequently, cationic polymers have long been used as conditioners in nail and skin care formulations. The substantivity of the cationic polymers for negatively charged skin and nails leads to film formation that facilitates lubricity, moisturizing and feel. Two commercially used cationic polymers are Merquat 550 (Calgon), a copolymer of acrylamide and dimethyldiallylammonium chloride, and polymer JR (Union Carbide), a quaternary nitrogen-containing hydroxyethyl cellulose.

It is a feature of the dual cationic terpolymers of the present invention that by providing different types of cationic components coexisting at the same time in the overall terpolymer, it is possible to adjust the cationic nature of the resulting polymer. By altering the mole percent charge, distribution of the cationic charge on the polymer backbone, and distance from the backbone (side chain length), one can achieve variations in the lubricity, moisturizing and feel of the resulting dual cationic terpolymer.

When cationic polymers are added to skin care products which are cleaning composition, e.g., dishwashing liquids, that contain anionic surfactants, formation of highly surface active association complexes takes place which imparts improved foam stability to the product. Maximum surface activity and foam stability, or lather, are achieved at near stoichiometric ratios of anionic sufactant:cationic polymer, where the complex is least water soluble. All cationic conditioners exhibit some incompatibility at some of these ratios. While compatibility gives clear formulations, where that is desired, a certain amount of incompatibility is also acceptable.

The skin and nail conditioning properties of lubricity, moisturizing and feel, are related to the film forming properties of the cationic monomers, as well as to molecular weight, with performance increasing with increasing molecular weight.

The dual cationic terpolymers of the present invention give one the ability, by varying the proportions and individual character of the cationic, as well as acrylamide components, to balance the hydrophobic and hydrophilic characteristics of the overall dual cationic terpolymer, thereby permitting one to optimize the conditioning properties of the final product.

While all of the conditioning property improvements described above are applicable primarily to skin care, human nail care products will also benefit from the improvement in conditioning properties afforded by the dual cationic terpolymers of the present invention. In addition, fragile or brittle nails will be strengthened or hardened, and the appearance of the nails will be improved as a result of use of the dual cationic terpolymers of the present invention.

Thus, overall the dual cationic terpolymers of the present invention are believed to constitute a significant improvement in the skin and nail conditioning art because, when contrasted to the products heretofore used in the art, they exhibit a superior combination of skin and nail care properties. These properties include improved moisture retention, and improved lubricity and feel of the skin and nails during and after treatment.

2. Brief Description of the Prior Art

Heretofore, hair, skin and nail conditioning additives have been largely of three different types: cationic polymers, proteins or protein derivatives, and fatty quaternary ammonium compounds. Commonly used cationic polymers include: quaternary nitrogen-containing hydroxyethyl cellulose compounds, copolymers of vinylpyrrolidone and dimethylaminoethylmethacrylate, and amino functional polydimethylsiloxane. Hydrolyzed animal protein has been frequently used as a hair conditioner. Also used are natural products such as collagen and casein. Suitable quaternary ammonium compounds include such products as stearyl dimethyl ammonium chloride. A typical hair conditioning shampoo composition is described in U.S. Pat. No. 4,832,872. Hair wave-setting compositions for which a number of different cationic polymers are suggested are described in EP-A-0 270 250 and EP-A-0 246 090.

Conditioning additives comprising copolymers of dimethyldiallylammonium chloride and other monomers are well known; see, e.g., EP-A-0 308 189 (with acrylamide); EP-A-0 308 190 and U.S. Pat. No. 4,803,071 (with hydroxyethyl cellulose). The use of such polymers in cosmetics is also described in Sykes et al., *Drug Cosmet. Ind.*, 126(2), 62, 64, 66, 68, 136 (1980). EP-A-0 227 321 discloses copolymers of saccharides with cationic monomers used in making a mild soap bar.

The use of polymers of dimethyldiallylammonium chloride alone in hair treatment compositions is also known. See, e.g., U.S. Pat. No. 4,175,572 and 3,986,825.

While the use of various cationic polymers as additives for hair conditioning compositions has been suggested heretofore, there has been no appreciation that a significant improvement ,in all of the desired hair conditioning properties could be obtained by employing a dual cationic terpolymer of the type used in the compositions and methods of the present invention.

For example, U.S. Pat. No. 4,859,458 discloses hair conditioning polymers containing alkoxylated nitrogen salts of sulfonic acid which may also include additional monomers that may be neutral, anionic and/or cationic. While these include acrylamide, acrylic acid and dimethyldiallylammonium chloride, there is no suggestion of the dual cationic terpolymers of the present invention.

EP-A-0 353 987 discloses polymers for water-rinsable personal care products including conditioning shampoos, comprising a cationic monomer including dimethyldiallylammonium chloride, and other monomers. However, there is no suggestion of the dual cationic terpolymers of the present invention.

U.S. Pat. No. 4,710,374 and U.S. Pat. No. 4,842,849 both disclose compositions suitable for treating the hair comprising a cationic polymer including poly(dimethyldiallylammonium chloride), and other polymer materials, but there is no suggestion of the dual cationic terpolymers of the present invention.

EP-A-0 080 976 discloses aqueous hair-cosmetic compositions containing a surface active polymeric acrylic-based quaternary ammonium salt, a monomeric or oligomeric ammonium salt, and a surface active nonionic, anionic or zwitterionic component. The dual cationic terpolymers of the present invention are not suggested.

U.S. Pat. No. 4,128,631 discloses a method of imparting lubricity to keratinous substrates such as skin or hair by contacting said substrates with a salt of 2-acrylamide-methylpropane sulfonic acid (AMPSA) having a molecular weight of from 1–5 million. See also U.S. Pat. No. 4,065,422. The dual cationic terpolymers of the present invention and their unexpected advantageous properties are not suggested.

The dual cationic terpolymers of the present invention are regarded as novel compositions of matter because of their unique properties, and their use as hair, skin and nail conditioning additives has not heretofore been suggested.

Terpolymers of acrylamide/dimethyldiallymmonium chloride/acrylic acid are disclosed in U.S. Pat. No. 4,455,240; 4,460,477; 4,484,631; and 4,533,708; however, nowhere is there a suggestion of the dual cationic terpolymers of the present invention, or that those terpolymers might be used as conditioning additives for hair, skin or nail products.

A graft copolymer of acrylamide/acrylic acid/amylopectin/dimethyldiallylammonium chloride is disclosed in U.S. Pat. No. 4,131,576, but is only suggested for use as a pigment retention agent in papermaking.

The dual cationic terpolymers of the present invention represent a significant advance in the state of the hair, skin and nail conditioning art and afford properties which are a surprising improvement over those possessed by the conditioning additives in the prior art described above. In contrast to such additives, the dual cationic terpolymers of the present invention provide either an optimized combination of all conditioning properties, or else an optimized subset of such properties, which include, in the case of hair conditioning: detangling, wet combability, wet feel, dry combability, dry feel, sheen, static flyaway control, and curl retention; and in the case of skin and nail conditioning, include: nail strengthening and appearance improvement, retention of skin moisture, softening of the skin, attraction of air moisture, retardation of skin water loss, feel and reduction of skin irritations caused by contact with detergents, soaps and the like. A detailed demonstration of the dramatic improvement in these properties is set out further below.

SUMMARY OF THE INVENTION

The present invention relates to a composition for treating hair, skin and nails in which a cosmetically acceptable medium is used which contains from 0.1–10% by weight of a dual cationic terpolymer having a weight average molecular weight of from about 10 thousand to 10 million, comprising (a) from at least 30 to as much as 75 weight percent of acrylamide (AM), (b) from at least 25 to as much as 80 weight percent of the cationic monomer dimethyldiallylammonium chloride (DMDAAC), and (c) from at least 5 to as much as 35 weight percent of a second cationic monomer of the formula:

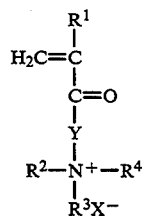

where Y is —O—A— or —NH—A—, where A is ethyl or propyl; $R^1$ is H or $CH_3$; $R^2$, $R^3$ and $R^4$ are independently selected from H and $C_{1-12}$alkyl; and $X^-$ is a suitable anion, especially $^-Cl$ and $^-OSO_3CH_3$.

In a preferred embodiment, the cosmetically acceptable medium is an anionic surfactant-containing shampoo, and the dual cationic terpolymer exhibits good compatibility therewith in that the final solution is clear.

The present invention also relates to a method of treating hair, skin and nails which comprises applying to said hair, skin and nails a cosmetically acceptable medium containing from 0.1–10% by weight of a dual cationic terpolymer having a weight average molecular weight of from about 10 thousand to 10 million, comprising (a) from at least 30 to as much as 75 weight percent of acrylamide (AM), (b) from at least 25 to as much as 80 weight percent of the cationic monomer dimethyldiallylammonium chloride (DMDAAC), and (c) from at least 5 to as much as 35 weight percent of a second cationic monomer of the formula:

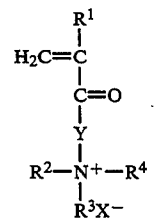

where Y is —O—A— or —NH—A—, where A is ethyl or propyl; $R^1$ is H or $CH_3$; $R^2$, $R^3$ and $R^4$ are independently selected from H and $C_{1-12}$alkyl; and $X^-$ is a suitable anion, especially $^-Cl$ and $^-OSO_3CH_3$.

In a preferred embodiment, the cosmetically acceptable medium is an anionic surfactant-containing shampoo, and the dual cationic terpolymer exhibits good compatibility therewith in that the final solution is clear.

DETAILED DESCRIPTION OF THE INVENTION

As already indicated, the present invention relates to a composition for treating hair in which a cosmetically acceptable medium is used which contains from 0.1–10% by weight of a dual cationic terpolymer having a weight average molecular weight of from about 10 thousand to 10 million, comprising (a) from at least 30 to as much as 75 weight percent of acrylamide (AM), (b) from at least 25 to as much as 80 weight percent of the cationic monomer dimethyldiallylammonium chloride (DMDAAC), and (c) from at least 5 to as much as 35 weight percent of a second cationic monomer of the formula:

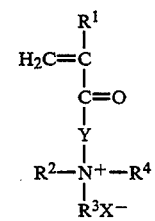

where Y is —O—A— or —NH—A—, where A is ethyl or propyl; $R^1$ is H or $CH_3$; $R^2$, $R^3$ and $R^4$ are independently selected from H and $C_{1-12}$alkyl; and $X^-$ is a suitable anion, especially $^-Cl$ and $^-OSO_3CH_3$.

COMPONENTS OF THE DUAL CATIONIC TERPOLYMERS

Turning to each of the components of the dual cationic terpolymer in turn, the nonionic monomer acrylamide may be represented by the following formula:

Acrylamide (AM)

-continued

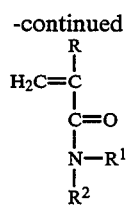

where R is H or $CH_3$; and $R^1$ and $R^2$ are independently H, $C_{1-4}$alkyl, $CH_2OCH_3$, $CH_2OCH_2CH(CH_3)_2$, $(CH_2CH_2O-)_x-H$, where $x=1-50$, or phenyl, or together are $C_{3-6}$cycloalkyl.

The preferred acrylamide monomer is the simplest, i.e., that where R, $R_1$, and $R_2$ are all H. However, the other acrylamide derivatives within the scope of the formula set out above are also contemplated to be a part of the present invention, since they are well known in the art of hair, skin and nail conditioning, where polyacrylamide and copolymers using acrylamide monomer are well known.

The nonionic acrylamide monomer portion of the dual cationic terpolymers of the present invention is present in an amount of from 30 to 75 weight percent of the total terpolymer. Preferably, this amount is from 40 to 60 weight percent, and most preferably, this amount is about 50 weight percent. The acrylamide contributes to the film forming capacity of the total terpolymer and thus improves curl retention of hair care products, and lubricity and feel of skin and nail care products. It also improves the static flyaway control of the overall terpolymer in hair care products.

The next component of the dual cationic terpolymers of the present invention is the first cationic monomer, i.e., derivatives of diallylamine, especially dimethyldiallylammonium chloride (DMDAAC), which may be represented by the following formula:

First Cationic Component: Diallylamines

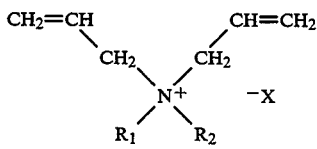

where $R_1$ and $R_2$ are independently H or $C_{1-12}$alkyl. The moiety $-X$ is a suitable anion, such as halide, preferably $-Cl$, but also including sulfate, and so forth. It is within the skill of the artisan to choose such an anion. The preferred first cationic monomer of the present invention is dimethyldiallylammonium chloride (DMDAAC), i.e., where $R_1$ and $R_2$ are $CH_3$.

The cationic dimethyldiallylammonium chloride monomer portion of the dual cationic terpolymers of the present invention is present in an amount of from 25 to 80 weight percent of the total terpolymer. Preferably, this amount is from 30 to 60 weight percent, most preferably about 40 weight percent. The dimethyldiallylammonium chloride contributes to all of the hair conditioning properties except for curl retention. As a cationic monomer it possesses the inherent substantivity necessary for the overall terpolymer to function. It also provides the basic improvement in detangling, wet and dry hair combability, sheen and feel, and control of static flyaway in hair care products. In skin and nail care products, the dimethyldiallylammonium chloride provides the basic improvement in moisturizing, lubricity, feel and nail strengthening. However the dimethyldiallylammonium chloride does not possess good film forming properties, and thus does not play any substantial role in improving curl retention in hair care products.

The final component of the dual cationic terpolymers of the present invention is the second cationic component, which may be represented by the following formula:

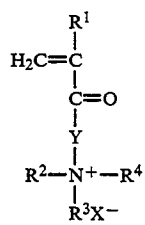

where Y is $-O-A-$ or $-NH-A-$, where A is ethyl or propyl; $R^1$ is H or $CH_3$; $R^2$, $R^3$ and $R^4$ are independently selected from H and $C_{1-12}$alkyl; and $X^-$ is a suitable anion, especially $-Cl$ and $-OSO_3CH_3$.

The second cationic monomer portion of the dual cationic terpolymers of the present invention is present in an amount of from 5 to 35 weight percent of the total terpolymer. Preferably, this amount is from 7 to 20 weight percent, most preferably about 10 weight percent. As with the dimethyldiallylammonium chloride cationic component, the second cationic component contributes to all of the hair conditioning properties except for curl retention. As a cationic monomer it possesses the inherent substantivity necessary for the overall terpolymer to function. It also provides the basic improvement in detangling, wet and dry hair combability, sheen and feel, and control of static flyaway in hair care products. In skin and nail care products, the second cationic component provides the basic improvement in moisturizing, lubricity, feel and nail strengthening. However, as with the dimethyldiallylammonium chloride component, the second cationic component does not possess good film forming properties, and thus does not play any substantial role in improving curl retention in hair care products.

It has been found that surprisingly, the second cationic component of the terpolymers of the present invention, rather than merely cumulatively providing the same properties as conferred by the first cationic component, i.e., the dimethyldiallylammonium chloride component, affords properties which are an unexpected improvement over those possessed by the hair, skin and nail conditioning additives in the prior art described further above. In contrast to such additives, the dual cationic terpolymers of the present invention provide either an optimized combination of all hair conditioning properties, or else an optimized subset of such properties.

In accordance with the present invention, there are certain preferred species of the second cationic component of the terpolymers which may be used. These are as follows:

Where $Y=-O-A-$; and :

A=ethylene; $R^{1-4}$=methyl; $X^-$=chloro; the compound is methacryloxyethyl trimethylammonium chloride (METAC). An unquaternized form of this cationic monomer is that where one of $R^{2-4}$ is hydrogen, giving dimethylaminoethyl methacrylate (DMAEM), which is hydrolyzed to form a cationic species.

A=ethyl; $R^1$=hydrogen; $R^{2-4}$=methyl; $X^-$=chloro; the compound is acryloxyethyl trimethylammonium chloride (AETAC).

$X^-$=methylsulfate ($OSO_3CH_3$), and the other substituents are as above, the compounds are methacryloxyethyl trimethylammonium methylsulfate (METAMS) and acryloxyethyl trimethylammonium methylsulfate (AETAMS).

Where Y=—NH—A—; and:

A=propyl; $R^{1-4}$=methyl; $X^-$=chloro; the compound is methacrylamidopropyl trimethylammonium chloride (MAPTAC). An unquaternized form of this cationic monomer is that where one of $R^{2-4}$ is hydrogen, giving dimethylaminopropyl methacrylamide (DMAPMA), which is hydrolyzed to form a cationic species.

SPECIFIC DUAL CATIONIC TERPOLYMERS

Examples of specific preferred dual cationic terpolymers within the scope of the present invention are the following:

| Monomer Components | Weight Percent Composition |
|---|---|
| AM/DMDAAC/ABTAC | 50/40/10 |
| AM/DMDAAC/DMAEM | 50/40/10 |
| AM/DMDAAC/MAPTAC | 50/40/10 |
| AM/DMDAAC/DMAPMA | 50/40/10 |
| AM/DMDAAC/METAMS | 50/40/10 |
| AM/DMDAAC/AETAC | 50/40/10 |

Molecular Weights

The molecular weight of the dual cationic terpolymers of the present invention may be within the broad range of from about 10 thousand to about 10 million. The molecular weights of most of the specific terpolymers described herein are within the range of about 4 to 8 million. However, it is generally conceded that for polymers used in skin and nail conditioning, molecular weights over about 1 million add little to the effectiveness of those polymers in terms of conditioning properties. At the other end of the scale, polymers with relatively low molecular weights may also be effective in providing skin and nail conditioning properties. The dual cationic terpolymers of the present invention are also useful in weight average molecular weight ranges below 1 million, and even below 100 thousand, although generally the preferred molecular weight range will be from about 500 thousand to 5 million.

Reduced viscosity (dl/g) is used herein as an approximate measure of the weight average molecular weight of the dual cationic terpolymers of the present invention. Such values represent a capillary viscosity measured with a Ubbelohde Capillary Viscometer at 0.05% concentration of polymer in a 1M NaCl solution, pH 7, at 30° C. The resulting value is calculated in accordance with methods well known in the art.

Preparation (Polymerization)

The dual cationic terpolymers of the present invention may be prepared in a straightforward manner by using the process described immediately below.

For each terpolymer composition the appropriate weights of aqueous acrylamide component, and cationic component, e.g., DMDAAC, monomers are charged to a glass reactor equipped with stirring. The volume of second cationic component, e.g., MAPTAG, monomer to be added is diluted first with deionized water and then added to the reactor with vigorous stirring to give a total monomer concentration of 14–20%. The monomer mixture is adjusted to pH 6.5 with dilute NaOH, heated to 55° C., and purged with nitrogen for at least thirty minutes. Polymerization is initiated by adding $5\times10^{-2}$ mole % of sodium persulfate and $2.4\times10^{-3}$ mole % of sodium bisulfite. After the peak exotherm is reached, additional dilution water and sodium bisulfite are added to scavenge any residual monomer and to dilute the final product to 4–8% polymer solids.

COSMETICALLY ACCEPTABLE MEDIA

The dual cationic terpolymers of the present invention are used as compositions for treating human hair, skin and nails by incorporating them in a cosmetically acceptable medium in amounts of from 0.1–10% by weight of said terpolymer, and preferably in an amount of from 0.5 to 5% by weight of said terpolymer.

These compositions can be presented in various forms, i.e., various cosmetically acceptable media, such as a liquid, cream, emulsion, gel, thickening lotion or powder; they can contain water and also any cosmetically acceptable solvent, in particular monoalcohols, such as alkanols having 1 to 8 carbon atoms, like ethanol, isopropanol, benzyl alcohol and phenylethyl alcohol, polyalcohols, such as alkylene glycols, like glycerine, ethylene glycol and propylene glycol, and glycol ethers, such as mono-, di- and tri-ethylene glycol monoalkyl ethers, for example ethylene glycol monomethyl ether, ethylene glycol monomethyl ether and diethylene glycol monomethyl ether, used singly or in a mixture. These solvents can be present in proportions of up to as much as 70% by weight, relative to the weight of the total composition.

These compositions can also be packaged as an aerosol, in which case they can be applied either in the form of an aerosol spray or in the form of an aerosol foam.

As the propellant gas for these aerosols, it is possible to use, in particular, dimethyl ether, carbon dioxide, nitrogen, nitrous oxide and volatile hydrocarbons, such as butane, isobutane, propane and, possibly, chlorinated and fluorinated hydrocarbons, although the latter are falling into increasing environmental disfavor.

Preferred compositions can also contain electrolytes, such as aluminum chlorhydrate, alkali metal salts, e.g., sodium, potassium or lithium salts, these salts preferably being halides, such as the chloride or bromide, and the sulphate, or salts with organic acids, such as the acetates or lactates, and also alkaline earth metal salts, preferably the carbonates, silicates, nitrates, acetates, gluconates, pantothenates and lactates of calcium, magnesium and strontium.

These compositions can also be presented in the form of a powder or of lyophilisates to be diluted before use.

The compositions according to the present invention can contain any other ingredient normally used in cosmetics, such as perfumes, dyestuffs which can serve to color the composition itself or the skin and/or nails, preservatives, sequestering agents, thickeners, silicones, softeners, foam synergistic agents, foam stabilizers, sun filters, peptising agents and also anionic, non-ionic, cationic or amphoteric surface-active agents or mixtures thereof. A list of the surface-active agents which can be used according to the present invention is given in U.S. Pat. No. 4,240,450; 4,445,521; and 4,719,099.

Especially for Hair Care Products

The compositions according to the present invention can be used, in particular, in the form of a shampoo, a rinsing lotion, a cream or a treatment product which can be applied before or after coloring or bleaching, before or after shampooing, before or after perming or before or after straightening, and can also adopt the form of a coloring product, a setting lotion, a brushing lotion, a bleaching product, a perming product or a straightening product.

A particularly preferred embodiment consists of use in the form of a shampoo for washing the hair.

In this case, these compositions contain anionic, cationic, nonionic or amphoteric surface-active agents typically in an amount from 3 to 50% by weight, preferably 3 to 20%, and their pH is 3 to 10.

A list of the surface-active agents which can be used according to the invention is given in U.S. Pat. No. 4,240,450; 4,445,521; and 4,719,099.

Another preferred embodiment consists of use in the form of a rinsing lotion to be applied mainly before or after shampooing. These lotions are typically aqueous or aqueous-alcoholic solutions, emulsions, thickened lotions or gels. If the compositions are presented in the form of an emulsion, they can be nonionic, anionic or cationic. The nonionic emulsions consist mainly of a mixture of an oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially carbopol, xanthan gums, sodium alginates, gum arabic and cellulose derivatives, and it is also possible to achieve thickening by means of a mixture of polyethylene glycol stearate or distearate or by means of a mixture of a phosphoric acid ester and an amide. The concentration of thickener is suitably 0.05 to 15% by weight. If the compositions are presented in the form of a styling lotion, shaping lotion or setting lotion, they generally comprise, in aqueous, alcoholic or aqueous-alcoholic solution, the dual cationic terpolymers defined above.

If the compositions of the invention are intended for use in the dyeing of keratin fibers, and in particular human hair, they contain at least one oxidation dyestuff precursor and/or one direct dyestuff, in addition to the dual cationic terpolymer. They can also contain any other adjuvant normally used in this type of composition.

The pH of the dyeing compositions is generally 7 to 11 and can be adjusted to the desired value by adding an alkalizing agent.

The composition according to the present invention can also be used for waving or straightening the hair. In this case, the composition contains, in addition to the dual cationic terpolymer, one or more reducing agents and, if appropriate, other adjuvants normally used in this type of composition; such compositions are intended for use conjointly with a neutralizing composition.

Especially for Skin and Nail Care Products

If the compositions according to the present invention are presented in the form of a thickened lotion or a gel, they contain thickeners in the presence or absence of a solvent. The thickeners which can be used are especially carbopol, xanthan gums, sodium alginates, gum arabic and cellulose derivatives, and it is also possible to achieve thickening by means of a mixture of polyethylene glycol stearate or distearate or by means of a mixture of a phosphoric acid ester and an amide. The concentration of thickener is suitably 0.05 to 15% by weight.

The pH of the dyeing compositions is generally 7 to 11 and can be adjusted to the desired value by adding an alkalizing agent.

As already mentioned, all alcohols and particularly the monohydric alcohols may be used as ingredients with the dual cationic terpolymers of the present invention. Alcohols ($C_1$–$C_{24}$) which are non-irritating to the skin such as methanol, ethanol, isopropanol, propyl, lauryl, myristyl, cetyl, and stearyl, as well as mixtures thereof, may be used. Polyols such as glycerine, or ethylene glycol or propylene glycol may be utilized advantageously with the dual cationic terpolymers of the present invention. The choice of the alcohol to be utilized with the particular terpolymer of the present invention will ordinarily be dictated by product aesthetics and the physical form of the composition. For instance, where liquid compositions are desired, the lower alcohols are preferably utilized, while solid or cream compositions within the scope of the present invention will normally require the higher alcohols. Where the skin and nail care formulations of the present invention contain ingredients other than the dual cationic terpolymer or the alcohol in substantial amounts, the choice of the particular alcohol becomes less important. For example, if the skin and nail care product is to be an abrasive hand cleaning product, then a large proportion of the product will be surface active agents and an abrasive, such as pumice or sand, thereby giving wide latitude to the choice of the particular alcohol.

A desirable variable of the present invention is the incorporation of water with the dual cationic terpolymer of the present invention. A resultant increase in viscosity of the water is noted with no adverse effects on the stability of the product. Thus, water is a highly suitable carrier which may be used as a vehicle for contacting the dual cationic terpolymer and the skin or nail substrate. The particular weight ratios at which the desirable increase in viscosity occurs for mixtures of the ampholyte terpolymer and water are respectively from about 1:10,000 to about 1:100. Preferably this ratio is in the range of from about 1:1000 to about 1:5000. Within the aforementioned range, highly viscous skin and nail care compositions are obtained with low solids content. Such compositions are desirable in that they allow compositions such as suntan or body lotions to be formulated in a thickened state, providing greater ease of application.

In the present invention the dual cationic terpolymer is ordinarily used at a level of about 0.001 gram per square centimeter to about 0.1 gram per square centimeter of the affected substrate.

The moisturizing, lubricating and other conditioning effects of the dual cationic terpolymers of the present invention may be obtained through using such diverse products as soap bars, dishwashing compositions, douches, hand and body lotions, suntan lotion, cold creams, preshave and after shave products, as well as cleansing or lotion pads and wound dressings, deodorant and antiperspirant products in stick, gel, lotion and aerosol forms, cosmetics including lipstick, rouge, mascara and eye liner, facial bases and powders, wrinkle and spot removing creams and lotions, and the like, and many other skin and nail care products. Listed below are materials which may be included in such skin and nail care products.

Hand and body lotions frequently contain emollients such as stearic acid, glycerol monostearate, mineral oil, glycerine, sesame oil, bees wax, lauryl, myristyl, cetyl or stearyl alcohols, lanolin, lecithin, sterols, isopropyl-myristate, as well any other recognized emollients. Emollients are typically used in the compositions of the present invention at levels of from abut 1% to about 50% by weight.

Astringents and antiseptics may be incorporated into the compositions of the present invention. A preferred astringent material is zinc phenolsulfonate. The foregoing material exhibits not only astringent but also antiseptic qualities and is of particular use in preshave formulations to stiffen the beard. Humectants such as propylene glycol are also desirable ingredients for inclusion in skin and nail care products to prevent drying of the skin. Allantoin is included in such compositions for its soothing and healing effects upon injured skin.

The soap bar and dishwashing compositions of the present invention may contain all manner of anionic, nonionic, zwitterionic, amphoteric or cationic surfactants. Typically the surfactant will be present at from about 1% to about 70%, preferably about 3% to 35% by weight.

Most preferably, the dishwashing compositions of the present invention contain anionic surfactants which, for example, include alkylether sulfates, olefin sulfonates, alkyl and alkenyl sulfates, alkyl sulfonates, and alkylbenzene sulfonates. A particularly useful discovery is that the dual cationic terpolymer, when used with a surface active agent, enhances and prolongs suds life. Consumers using dishwashing products often tend to overuse the composition when the suds disappear from the surface of the dishpan. Thus, in the surfactant formulations of the present invention, the presence of the dual cationic terpolymer maintains the suds level, thus avoiding inadvertent overuse of the product by the consumer.

The soap bars of the present invention may either contain real soap, combinations of soap and synthetic surfactants, or may be formulated solely with synthetic surfactants, such as alkylbenzene sulfonates. For a more detailed disclosure of components which are ordinarily found either as surfactants or additives in dishwashing compositions, see U.S. Pat. No. 3,963,649.

EXAMPLES OF PREFERRED EMBODIMENTS

The following examples demonstrate hair and skin conditioning improvement results which can be obtained with specific dual cationic terpolymers of the present invention, but are not intended to in any way limit the scope of the present invention.

HAIR CARE PRODUCTS

EXAMPLE 1

Wet Hair: Detangling, Combability and Feel

The following procedures can be used to evaluate wet hair detangling, combability and feel:
1. Eighteen 2 grams tresses of bleached hair (supplied by Ruth L. Weintraub Co., Inc., 420 Madison Avenue, New York, N.Y. 10017), 8 inches in length, are prepared for testing. The ends are trimmed to equal lengths (6 inches; length =L); and the root end of the hair is placed into a clamp.
2. All of the tresses are washed in clean denatured alcohol (100%), by dipping each tress in the denatured alcohol and swirling 3 times. The tresses are allowed to dry by hanging on a peg board, at room temperature for 1 hour.
3. Using 6 tresses per treatment, each tress is immersed in one of the following three test solutions (the pH of these solutions is adjusted to 6.0±0.1 with citric acid or NaOH):
   a) Terpolymer solution, 0.5% Solids
   b) Gafquat 755N (Reg. TM) solution, 0.5% solids
   c) deionized (DI) water.
Each tress is allowed to soak in the solution for 3 minutes and is then rinsed under running deionized water for 2 minutes.
4. After the 2 minute rinse, each trees is evaluated for detangling, wet hair combability and wet hair feel. The detangling is evaluated by holding the clamp of the tress in one hand and using the other hand to comb the tress twice with the coarse end of the comb. The tress is then combed 5 times to remove all the tangles and the tress is combed twice with the fine end of the comb to evaluate wet hair comb. The tresses are evaluated and rated for detangling and wet hair combability in accordance with the following scale:
4=Excellent=No snags
3=Very Good=Very few snags
2=Good=Few snags
1=Fair=Many snags
0=Poor=Very many snags The wet hair feel is evaluated by the subjective feel to the fingers of each tress. The combs [Goody (Reg. TM), H. Goodman & Sons, Inc., New York 10001] used for these tests are $7\frac{1}{4}'' \times 1\frac{1}{2}''$. The teeth on the course end of the comb are spaced $\frac{1}{8}''$ apart and the teeth on the fine end of the comb are spaced 1/16" apart.

EXAMPLE 2

Curl Retention

After the procedures are carried out as described in Example 1, the following procedures are used to evaluate curl retention:
5. A "curl paper" [Goody (Reg. TM), H. Goodman & Sons, Inc., N.Y. 10001] is folded around each hair tress, close to the clamp, and slid down the hair to cover all loose ends. The end of the hair tress is set on the left edge of the roller [medium snap-over roller 11/16" diameter, Sekine (Reg. TM) Corporation, New York, N.Y. 10003], and is wound three times around the roller so that it ended up on the right hand edge of the roller. When all of the tresses had been treated, the entire rack of tresses is placed in a 50% relative humidity room and allowed to set overnight (at least 12 hours).
6. After this 12 hour set period, a humidity chamber is placed in a 50% relative humidity room. The atmosphere in the humidity chamber is then raised to 70% relative humidity (approx. 30 minutes) by blowing air over a 20% (w/w) solution of aqueous ammonium chloride and into the humidity chamber.
7. The rollers are then removed from the tresses.

8. The initial lengths of all the tresses are recorded as the length from the clamp to the bottom of the curl (initial length=$L_o$).
9. The rack of curls is then placed in the humidity chamber at 70% relative humidity for 15 minutes.
10. The length ($L_t$) of each tress (from the clamp to the bottom of the curl) is then measured every 15 minutes for 2 hours.
11. The curl retention is calculated using the following formula:

$$\% \text{ Curl Retention} = \frac{L - L_t}{L - L_o} \times 100$$

EXAMPLE 3

Dry Hair: Combability, Feel and Sheen

The following procedures, which followed those carried out as described above in Examples 1 and 2, are used to evaluate dry hair combability, feel and sheen:

12. The rack of tresses used for the curl retention evaluations described in the previous example is removed from the humidity chamber and placed on a lab bench. Then, 8 panelists evaluated the 3 sets of 6 tresses for "ease of dry combing," "feel of hair," and "sheen or luster." Each panelist rated each tress for the preceding categories according to the following rating scale:
Poor=0; Fair=1; Good=2; Very Good=3; Excellent=4.

EXAMPLE 4

Static Flyaway Control

The following procedures, which followed those carried out as described above in Examples 1, 2 and 3, are used to evaluate control of static flyaway:

13. When the preceding panelist evaluations are complete, one tress from each set (1-terpolymer, 1-Gafquat and 1-DI water) is wet under running DI water and combed until no tangles remained. These tresses are placed on a smaller peg board and put in the 50% relative humidity room overnight.
14. Each of the tresses is then placed on a peg board in front of a protractor. The tresses are combed 20 times, with the same stroke each time, and the angle of the hair is recorded. The static angle of the hair is determined by the hair strand which produced the largest angle for that tress.

The following examples illustrate various cosmetically acceptable media for preparing hair care compositions using the dual cationic terpolymers of the present invention. In those Examples, the following terpolymer abbreviations are used:

| Dual Cationic A: | | |
|---|---|---|
| By weight: | 50% Acrylamide = | Sample |
| | 40% DMDAAC | No. XX |
| | 10% DMAEM | |
| Dual Cationic B: | | |
| By weight: | 50% Acrylamide = | Sample |
| | 25% DMDAAC | No. YY |
| | 25% DMAEM | |
| Dual Cationic C: | | |
| By weight: | 50% Acrylamide = | Sample |
| | 40% DMDAAC | No. ZZ |
| | 10% MAPTAC | |

EXAMPLE 5

Creme Rinse

| WT. % | INGREDIENT |
|---|---|
| 93.1 | $H_2O$ |
| 1.2 | Cetyl Alcohol |
| 0.8 | Stearyl Alcohol |
| 1.0 | Sorbitan Oleate |
| 0.4 | Polysorbate-85 |
| 1.0 | Distearyldiammonium Chloride |
| 2.5 | Dual Cationic B |

In this formulation, the dual cationic terpolymer stabilized an otherwise unstable composition. The dual cationic terpolymer also improved combability, hair feel, and provided a feeling of increased hair body. Similar results would be expected at dual cationic terpolymer concentrations of 0.1 to 10.0% by weight.

EXAMPLE 6

Shampoo

| WT. % | INGREDIENT |
|---|---|
| 28.50 | Water |
| 32.30 | Ammonium Lauryl Sulfate |
| 31.40 | Ammonium Laureth Sulfate |
| 4.25 | Ammonium Dodecylbenzene Sulfonate |
| 3.40 | Lauramide DEA |
| 0.15 | Disodium EDTA |
| 3.0 | Dual Cationic A |

The dual cationic terpolymer in this product formulation is responsible for a better feeling shampoo with thicker feeling lather. The hair is easier to comb and had a feeling of greater body. Similar results would be expected at dual cationic terpolymer concentrations of 0.1 to 10.0% by weight.

EXAMPLE 7

Creme Type Rearranger

| WT. % | INGREDIENT |
|---|---|
| 68.95 | $H_2O$ |
| 6.00 | Sodium Lauryl Sulfate |
| 7.90 | Cetearyl Alcohol and Ceteareth-20 |
| 6.00 | Cetyl Alcohol and Ceteareth-30 |
| 1.50 | Ethylene Glycol Monostearate |
| 0.15 | Sodium Dihydroxyethylglycinate |
| 7.50 | Ammonium Thioglycolate (60%) |
| 2.00 | Aqua Ammonia |
| 4.00 | Dual Cationic C |

This type of product formulation is applied to extremely curly hair and is combed into the hair. Hair treated in this way will be straightened. The presence the dual cationic terpolymer makes the hair noticeably easier to comb. Effective amounts of dual cationic terpolymer in this type of product will be from 0.20% to 15.00% by weight.

EXAMPLE 8

Hair Styling Glaze

| WT. % | INGREDIENT |
|---|---|
| 88.4% | Water |
| 1.10 | Hydroxypropyl Methylcellulose |

-continued

| WT. % | INGREDIENT |
|---|---|
| 0.50 | Quaternium-80 |
| 10.00 | Dual Cationic B |

The dual cationic terpolymer in this formulation provides curl and style retention, and the dual cationic terpolymer should be effective for this purpose at concentrations of 0.5% to 20.0% by weight.

EXAMPLE 9

Permanent Wave Neutralizer

| WT. % | INGREDIENT |
|---|---|
| 91.92 | H$_2$O |
| 0.20 | Pentasodium Pentatate |
| 0.180 | Citric Acid |
| 5.70 | Hydrogen Peroxide (35%) |
| 2.0 | Dual Cationic C |

The dual cationic terpolymer in this product formulation imparts conditioning to and improves combability of hair. The dual cationic terpolymer should be effective at concentrations of 0.1% to 10% by weight or more.

EXAMPLE 10

Hair Spray

| WT. % | INGREDIENT |
|---|---|
| 92.00 | Water |
| 1.00 | Acetamide MEA |
| 1.00 | Glycerin |
| 3.00 | Vinylcaprolactam/PVP/Dimethylaminoethylmethacrylate polymer |
| 3.00 | Dual Cationic A |

The dual cationic terpolymer in this formulation increases the style holding properties while improving the flexibility of the second polymer. Similar results are obtained at dual cationic terpolymer concentrations of 0.3% to 10.0% by weight.

EXAMPLE 11

Hair Styling Gel

| WT. % | INGREDIENT |
|---|---|
| 91.75 | H$_2$O |
| 0.375 | Carbomer - 940 |
| 0.625 | Triethanolamine |
| 0.10 | Trisodium EDTA |
| 5.0 | PVP |
| 0.2 | Laureth 23 |
| 0.2 | Oleth 20 |
| 0.25 | Hexylene Glycol |
| 1.50 | Dual Cationic A |

The dual cationic terpolymer in this product formulation provides increased curl and style retention along with increased flexibility of the hair fixative film.

SKIN CARE PRODUCTS

EXAMPLE 12

Each dual cationic terpolymer is evaluated sequentially for feel during use, feel during rinse off and feel after application. Performance is evaluated by independent observers on coded samples using ratings of 0 to 4 (poor to excellent).

Each dual cationic terpolymer (1 wt %) is blended with a commercial product and evaluated by feel. One hand of each observer is treated with 1 gram of commercial liquid soap and at the same time the other hand of each observer is treated with 1 gram of commercial product plus 1 wt % polymer. Simultaneously, the observers rate the feel of the products. For liquid soaps, the feel during wash, during rinse, and after treatment are evaluated. For hand lotions, both hands of each observer are treated with each formulation and compared to its previously evaluated untreated commercial hand lotion. The feel during application and after application is evaluated using again a rating of 0 to 4 (poor to excellent).

In addition to feel, moisture vapor transmission rates (MVTR) are determined; 3 mil films on laboratory paper toweling are prepared with the dual cationic terpolymers. Each film is attached to a glass container holding a desiccant, anhydrous CaCl$_2$, and placed in 92 to 96% RH at 86° F. The MVTR results indicate a high rate of water vapor transmission.

The percent pickup of air moisture is also determined for the dual cationic terpolymers. A 2.2 mil film of terpolymer on laboratory paper toweling will pick up a certain percentage of moisture at 86° F., 92 to 96% relative humidity in 24 hours. The laboratory paper, by itself, will have essentially no pickup of air moisture. The polymer film will have a soft, smooth feel both dry and after moisture pickup. This data indicates that the dual cationic terpolymers of the present invention function as humectants.

The following dual cationic terpolymers, when evaluated in accordance with the assays and tests described above, will be found to give good to excellent results:

| Polymer Composition (Weight Percent) | | |
|---|---|---|
| AM | DMDAAC | DMAEM |
| 50 | 40 | 10 |
| 50 | 25 | 25 |
| AM | DMDAAC | MAPTAC |
| 50 | 40 | 10 |
| 50 | 25 | 25 |
| AM | DMDAAC | AETAC |
| 50 | 40 | 10 |
| 50 | 25 | 25 |
| 50 | 10 | 40 |

The following examples illustrate various cosmetically acceptable media for preparing skin and nail care compositions using the dual cationic terpolymers of the present invention. In those Examples, the following terpolymer abbreviations are used:

| Polyampholyte A: | |
|---|---|
| By weight: | 50% Acrylamide |
| | 40% DMDAAC |
| | 10% DMAEM |
| Polyampholyte B: | |
| By weight: | 50% Acrylamide |
| | 25% DMDAAC |
| | 25% DMAEM |
| Polyampholyte C: | |
| By weight: | 50% Acrylamide |
| | 40% DMDAAC |
| | 10% MAPTAC |

EXAMPLE 13

After Shave

| WT. % | INGREDIENT |
|---|---|
| 47.5% | SDA 40 Alcohol |
| 3.0% | Propylene Glycol |
| 0.5% | Dual Cationic A |
| 48.0% | H₂O |
| 1.0% | Fragrance |

The addition of the dual cationic terpolymer to this formula will leave the skin with a soft silky feeling during application and a soft moist feeling after dry-down. Substantially, the same results will be obtained if the terpolymer concentration is varied between 0.1% and 5.0%.

EXAMPLE 14

Sunscreen

| WT. % | INGREDIENT |
|---|---|
| 5.00 | Octyl Dimethyl PABA |
| 5.00 | Octyl Methoxycinnamate |
| 4.00 | Glyceryl Stearate |
| 4.00 | Sorbitan Sesquioleate |
| 4.00 | Lanolin |
| 3.00 | C12-15 Alcohols Benzoate |
| 3.0 | Cocoa Butter |
| 0.5 | Jojoba Oil |
| 0.5 | Benzyl Alcohol |
| 0.5 | Dimethicone |
| 2.0 | Stearic Acid |
| 0.1 | Carbomer-941 |
| 62.3 | Water |
| 1.40 | Dual Cationic B |
| 0.10 | Disodium EDTA |
| 0.50 | Triethanolamine |
| 4.0 | Sorbitol |
| 0.1 | Tocopheryl Acetate |

Adding the dual cationic terpolymer to this formula will improve the feel of the product and provide a softer feeling to the skin after application.

EXAMPLE 15 and Lotion

| WT. % | INGREDIENT |
|---|---|
| 7.00 | Stearic Acid |
| 0.50 | C12-15 Alcohols Benzoate |
| 0.50 | Sorbitan Oleate |
| 2.50 | Polysorbate 60 |
| 10.0 | Sorbitol |
| 1.50 | Dual Cationic C |
| 78.00 | Water |

The dual cationic terpolymer will provide a softer, smooth feel to the dry skin. Similar results can be expected at dual cationic terpolymer concentrations of 0.2 to 10.0%.

EXAMPLE 16

Liquid Hand Soap

| WT. % | INGREDIENT |
|---|---|
| 65.09 | H₂O |
| 22.0% | Sodium C14-16 Olefin Sulfonate |
| 3.0 | Cocamidopropyl Betaine |
| 3.0 | Lauramide DEA |
| 0.53 | Chloroxylenol |
| 0.13 | Tetrasodium EDTA |
| 2.00 | Sodium Chloride |
| 0.25 | Citric Acid |
| 4.00 | Dual Cationic A |

The dual cationic terpolymer in this product will provide a richer feeling liquid soap and lather, and after rinsing, the skin will be noticeably softer and smoother. Similar properties will be obtained using dual cationic terpolymer concentrations of 0.1 to 10.0%.

EXAMPLE 17

Bath Oil Bar

| WT. % | INGREDIENT |
|---|---|
| 2.00 | Water |
| 10.00 | Propylene Glycol |
| 1.00 | Dual Cationic B |
| 69.00 | PPG-3 Myristyl Ether |
| 10.00 | Mineral Oil |
| 8.00 | Sodium Stearate |

The dual cationic terpolymer in this product will result in better skin feel after use. Similar results will be obtained using 0.1 to 10% dual cationic terpolymer.

EXAMPLE 18

Brushless Shaving Cream

| WT. % | INGREDIENT |
|---|---|
| 18.00 | Stearic Acid |
| 4.00 | Ethylene Glycol Monostearate |
| 4.00 | Lanolin Alcohol |
| 4.00 | C12-15 Alcohols Benzoate |
| 2.00 | Glycerin |
| 1.00 | Triethanolamine |
| 2.50 | Dual Cationic C |
| 64.50 | H₂O |

The dual cationic terpolymer will provide a creamier product with more slip and leave the skin feeling softer. Similar results will be obtained at dual cationic terpolymer concentrations of 0.3 to 7.5%.

What is claimed is:

1. A composition for treating hair, skin and nails in which a cosmetically acceptable medium is used which contains from 0.1-10% by weight of a dual cationic terpolymer having a weight average molecular weight of from about 10 thousand to 10 million, said terpolymer consisting essentially of:
   (a) from at least 30 to as much as 75 weight percent of acrylamide (AM),
   (b) from at least 25 to as much as 80 weight percent of the cationic monomer dimethyldiallylammonium chloride (DMDAAC), and
   (c) from at least 5 to as much as 35 weight percent of a second cationic monomer of the formula:

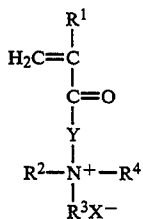

where Y is —O—A— or —NH—A—, where A is ethyl or propyl; $R^1$ is H or $CH_3$; $R^2$, $R^3$ and $R^4$ are independently selected from H and $C_{1-12}$alkyl; and $X^-$ is an anion.

2. A composition according to claim 1 wherein the cosmetically acceptable medium is an anionic surfactant-containing shampoo.

3. A composition according to claim 1 wherein the weight percent, based on the weight of said terpolymer, of AM is from 40 to 60, the weight percent of DMDAAC is from 30 to 60, and the weight percent of the second cationic component is from 7 to 20.

4. A composition according to claim 1 wherein the dual cationic terpolymer is selected from the group consisting of, based on the weight of said terpolymer:
1) 50 weight percent of AM, 40 weight percent of DMDAAC and 10 weight percent of dimethylaminoethyl methacrylate (DMAEM);
2) 50 weight percent of AM, 25 weight percent of DMDAAC and 25 weight percent of DMAEM;
3) 50 weight percent of AM, 40 weight percent of DMDAAC, and 10 weight percent of methacrylamidopropyl trimethylammonium chloride (MAPTAC); and
4) 50 weight percent of AM, 25 weight percent of DMDAAC, and 25 weight percent of MAPTAC.

5. A method of treating hair, skin and nails which comprises applying to said hair, skin and nails a cosmetically acceptable medium containing from 0.1–10% by weight of a dual cationic terpolymer having a weight average molecular weight of from about 10 thousand to 10 million, said terpolymer consisting essentially of, based on the weight of said terpolymer
(a) from at least 30 to as much as 75 weight percent of acrylamide (AM),
(b) from at least 25 to as much as 80 weight percent of the cationic monomer dimethyldiallylammonium chloride (DMDAAC), and
(c) from at least 5 to as much as 35 weight percent of a second cationic monomer of the formula:

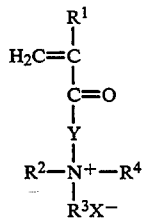

where Y is —O—A— or —NH—A—, where A is ethyl or propyl; $R^1$ is H or $CH_3$; $R^2$, $R^3$ and $R^4$ are independently selected from H and $C_{1-12}$alkyl; and $X^-$ is an anion.

6. A method according to claim 5 wherein the cosmetically acceptable medium is an anionic surfactant-containing shampoo.

7. A method according to claim 5 wherein the weight percent, based on the weight of said terpolymer, of AM is from 40 to 60, the weight percent of DMDAAC is from 30 to 60, and the weight percent of the second cationic component is from 7 to 20.

8. A method according to claim 5 wherein the dual cationic terpolymer is selected from the group consisting of, based on the weight of said terpolymer:
1) 50 weight percent of AM, 40 weight percent of DMDAAC and 10 weight percent of dimethylaminoethyl methacrylate (DMAEM);
2) 50 weight percent of AM, 25 weight percent of DMDAAC and 25 weight percent of DMAEM;
3) 50 weight percent of AM, 40 weight percent of DMDAAC, and 10 weight percent of methacrylamidopropyl trimethylammonium chloride (MAPTAC);
4) 50 weight percent of AM, 25 weight percent of DMDAAC, and 25 weight percent of MAPTAC;
5) 50 weight percent of AM, 40 weight percent of DMDAAC, and 10 weight percent of acryloxyethyl trimethylammonium chloride (AETAC);
6) 50 weight percent of AM, 25 weight percent of DMDAAC, and 25 weight percent of AETAC; and
7) 50 weight percent of AM, 10 weight percent of DMDAAC, and 40 weight percent of AETAC.

* * * * *